US007067246B1

(12) United States Patent
Zagury et al.

(10) Patent No.: US 7,067,246 B1
(45) Date of Patent: Jun. 27, 2006

(54) METHOD FOR DETERMINING PROGNOSIS OF HIV INFECTED INDIVIDUALS (75) Inventors: Daniel Zagury, Paris (FR); Jean-Francois Zagury, Paris (FR)

(73) Assignee: Neovacs S.A., Paris (FR)

( * ) Notice: Subject to any disclaimer, the term of this patent is extended or adjusted under 35 U.S.C. 154(b) by 0 days.

(21) Appl. No.: 09/763,369

(22) PCT Filed: Aug. 20, 1999

(86) PCT No.: PCT/US99/18770

§ 371 (c)(1),
(2), (4) Date: May 22, 2001

(87) PCT Pub. No.: WO00/11225

PCT Pub. Date: Mar. 2, 2000

Related U.S. Application Data (60) Provisional application No. 60/097,497, filed on Aug. 21, 1998.

(51) Int. Cl.
*C12Q 1/70* (2006.01)
(52) U.S. Cl. ..................... 435/5; 424/188.1; 424/208.1
(58) Field of Classification Search .................... 435/5, 435/7.1; 424/188.1, 208.1, 147.1
See application file for complete search history.

(56) References Cited

U.S. PATENT DOCUMENTS 5,108,891 A 4/1992 Croxson

FOREIGN PATENT DOCUMENTS

DE 195 14 089 A1 10/1996

OTHER PUBLICATIONS

Reiss, P., et al., 1991, "Contribution of anitbody response to recombinant HIV-1 gene-encoded products nef, rev, tat, and protease in predicting development of AIDS in HIV-1 infected individuals.", J. Acquir. Immune Defic. Syndr. 4:165-172.*
Franchini, G., et al., 1987, "Spectrum of natural antibodies against five HTLV-III antigens in infected individuals: correlation of antibody prevalence with clinical status.", Blood 69(2):437-441.*
Krone, W. J. A., et al., 1988, "Natural antibodies to HIV-tat epitopes and expression of HIV-1 genes in vivo.", J. Med. Virol. 26:261-270.*
Donovan, R. M., et al., 1996, "Changes in virus load markers during AIDS-associated opportunistic diseases in human immunodeficiency virus-infected persons.", J. Infect. Dis. 174:401-3.*
Pedersen, C., et al., 1992, "The effect of treatment with zidovudine with or without acyclovir on HIV p24 antigenaemia in patients with AIDS or AIDS-related complex.", AIDS 6:821-825.*
Molina, J.-M., et al., 1994, "Quantification of HIV-1 virus load under zidovudine therapy in patients with symptomatic HIV infection: relation to disease progression.", AIDS 8:27-33.*
Lafeuillade, A., et al., 1994, "Correlation between surrogate markers, viral load, and disease progression in HIV-1 infection.", J. Acquir. Immune Defic. Syndr. 7:1028-1033.*
Letvin, N., 1998, "Progress in the development of an HIV-1 vaccine.", Science 280:1875-1880.*
Johnston, M. I., 2000, "The role of nonhuman primate models in AIDS vaccine development.", Mol. Med. Today 6:267-270.*
Burton, D. R., and J. P. Moore, 1998, "Why do we not have an HIV vaccine and how can we make one?", Nature Med. Vaccine Suppl. 4(5):495-498.*
Lee, T.-H., 1997, "Acquired immunodeficiency disease vaccines: design and development.", in *AIDS: Biology, Diagnosis, Treatment and Prevention, fourth edition*, DeVita, V. T., et al., eds., Lippincott-Raven Publishers, pp. 605-616.*
Rodman, T. C., et al., 1992, "Human immunodeficiency virus (HIV) Tat-reactive antibodies present in normal HIV-negative sera and depleted in HIV-positive sera. Identification of the epitope", J. Exp. Med. 175:1247-1253.*
Zagury et al., "Antibodies to the HIV-1 Tat Protein Correlated With Nonprogression to AIDS: A Rationale for the Use of Tat Toxoid as an HIV-1 Vaccine," J. of Human Virology, May/Jun. 1998., vol. 1, No. 4, pp. 282-292.
Rodman et al., "Epitopes for Natural Antibodies of Human Immunodeficiency Virus (HIV)-negative(normal) and HIV-positive sera are coincident with two key functional sequences of HIV tat Protein," Proc. of Nat. Academy of Sciences, USA, Aug. 1993, vol. 90, pp. 7719-7723.
Rodman et al., "Natural Antibodies. Early hose defense against HIV? ," International Conf. on AIDS, 1992, vol. 8, No. 2, pp. A74 (abstract No. POA 2429).
Re et al., "Antibody Against Human Immunodeficiency Virus type 1 (HIV-1). Tat Protein may have influenced the progression of AIDS in HIV-1 infected hemophiliac patients," Clinical and Diagnostic Laboratory Immunology, Mar. 1996, vol. 3, No. 2, pp. 230-232.

(Continued)

*Primary Examiner*—Jeffrey S. Parkin
(74) *Attorney, Agent, or Firm*—Browdy and Neimark (57) ABSTRACT

The serum levels of anti-tat antibodies, tat protein, and p24 protein are predictive of disease progression in HIV infected individuals and serve as prognostic markers. The present invention relates to a method for determining the prognosis of an HIV infected individual by measuring serum levels of one or more of these prognostic markers. In addition, a method for monitoring whether an HIV infected individual is in need of immunization with a tat vaccine and a method for monitoring the efficacy of immunization with a tat vaccine are also disclosed.

2 Claims, 6 Drawing Sheets

OTHER PUBLICATIONS

Re et al., "Effect of Antibody to HIV-1 Tat Protein on Viral replication in vitro and progression of HIV-1 disease in vivo," *J. of Acquired Immune Deficiency Syndromes and Human Retrovirology*. Dec. 1, 1995, vol. 10, No. 4, pp. 408-416.

Rodman et al., "Human Immunodeficiency virus (HIV) Tat reactive antibodies present in normal HIV-negative sera and depleted in HIV-positive sera. Identification of the epitope," *J. of Experimental Medicine*. May 1, 1992, vol. 175, No. 5, pp. 1247-1253.

Gringeri et al., Safety and immunogenicity of HIV-1 Tat toxoid in immunocompromised HIV-1-infected patients, *Journal of Human Virology*, 1:293-298 (1998).

Reiss et al., Contribution of antibody response to recombinant HIV-1 gene-encoded products nef, rev, tat, and protease in prediciting development of AIDS in HIV-1-infected individuals, *Journal of Acquired Immune Deficiency Syndromes*, 4:165-172 (1991).

Gibellini et al., Antibody to HIV-1 tat protein, a key molecule in HIV-1 pathogenesis. A brief review, *Microbiologica*, 24:197-205 (20010.

* cited by examiner

METHOD FOR DETERMINING PROGNOSIS OF HIV INFECTED INDIVIDUALS

REFERENCE TO RELATED APPLICATIONS

The present application is the national stage under 35 U.S.C. 371 of international application PCT/US99/18770, filed Aug. 20, 1999, which designated the United States, which international application was published under PCT Article 21(2) in English.

BACKGROUND OF THE INVENTION

1. Field of the Invention

The present invention generally relates to diagnostic and prognostic tests for disease progression. More particularly, it relates to a prognostic test for the stage of progression of HIV infected patients and a method for treating HIV infected patients based on the prognosis.

2. Description of the Related Art

Following immune activation, HIV-1-infected CD4+ cells synthesize viral proteins and release virions (Zagury et al, 1986). In infected cells, the regulatory transactivating-transcription protein tat, which is not found in the viral particle, but is encoded by the HIV-1 genome, enhances the transcription of viral mRNA through interaction with the cis-acting RNA sequence termed TAR (Cullen, 1991). In contrast to its enhancing effect on viral replication, tat impairs the normal physiologic machinery of infected T cells, thus contributing to their premature death (Zagury et al, 1986). The tat-induced cellular alterations may also be exercised in uninfected T cells, since this protein, released from acutely infected cells into the extracellular compartment (Ensoli et al, 1993), can target uninfected cells by a mechanism involving interaction with integrins (Hynes, 1992) or other cell membrane receptors (Weeks et al, 1993). Immune cells, which carry a large density of integrin receptors, particularly after activation (Hynes, 1987), may be dysregulated by extracellular tat, as shown in vitro (Zagury et al, 1996). Pretreatment of activated PBMCs with tat induces both T cell immune suppression (Viscidi et al, 1995; Chirmule et al, 1995) and apoptosis (Li et al, 1995; Westendorp et al, 1995; Katsikis et al, 1997). Extracellular tat acts not only on T cells but also on antigen processing cells (APCs), e.g., monocytes, macrophages and dendritic cells (Zagury et al, 1998). The tat-induced immunosuppressive effect is further promulgated by the enhanced secretion of the immunosuppressive cytokine, IFN$\alpha$, by APCs (Zagury et al, 1998). The present inventors showed that PHA-activated PBMC cultures treated with HIV-1, but not untreated cultures, generate CD8$^+$ suppressive T cells. In this in vitro experimental model, the potent role of tat and IFN$\alpha$ in HIV-1-induced immune-suppression was confirmed since specific anti-tat and anti-IFN$\alpha$, but not control antibodies prevented the generation of CD8$^+$ suppressive T cells (Zagury et al, 1998).

Currently, the prognostic indicator or marker is viral load. However, the work of the present inventors shows that it is not a good prognostic indicator of future disease progression at an early stage of disease when the viral-load remains low, but is merely an indicator of the stage of disease (asymptomatic versus sick). While a test for the viral p24 protein is commercially available, this test is only used to determine whether an individual is infected, and not as a prognostic indicator/marker of disease progression.

Citation of any document herein is not intended as an admission that such document is pertinent prior art, or considered material to the patentability of any claim in the present application. Any statement as to content or a date of any document is based on the information available to applicants at the time of filing and does not constitute an admission as to the correctness of such a statement.

SUMMARY OF THE INVENTION

The present invention is based on the discovery that the immune parameters, tat protein, anti-tat antibody, and p24 protein levels, in HIV infected individuals are the best predictors of disease progression, at least at a non-advanced stage of disease. Using tat protein, anti-tat antibody, and p24 protein as prognostic markers, the present invention provides a method for determining the prognosis of an HIV infected individual by measuring the serum level of the prognostic marker and comparing it with either serum levels of the prognostic marker that are indicative of disease progression or non-progression or comparing it to a past measurement made earlier on the same individual.

The present invention also provides a method for treating an HIV infected individual by immunization with a tat vaccine when the monitoring of an individual's anti-tat antibody or tat protein level determines that a decrease in the level of anti-tat antibody or an increase in tat protein over time warrants the administration of tat vaccine.

Further provided is a method for evaluating the immune response of a non-infected individual as a result of immunization with a tat vaccine by measuring the level of anti-tat antibodies after immunization.

BRIEF DESCRIPTION OF THE DRAWINGS

FIGS. 4A–4F show scatterplots of anti-tat Ab levels (O.D.) versus: p24 antigen level (pg/ml) (p<0.001) (FIG. 4A); log$_{10}$ viral load (RNA copies/ml) (p=Not Significant or NS) (FIG. 4B); CD4 cell count (cells/mm$^3$) (p=NS) (FIG. 4C); anti-p24 Ab level (O.D.) (p=NS) (FIG. 4D); anti-nef Ab level (O.D.) (p=NS) (FIG. 4E); anti-TT Ab level (O.D.) (p=NS) (FIG. 4F) in sera of NP cases who remained stable (X) or progressed (▲) during the 21-month follow-up period. Dotted lines correspond to the median. Values in parentheses represent p-values, i.e., significance values obtained from Pearson correlation analyses.

FIGS. 5A and 5B show the kinetics of anti-Tat antibody (Ab) production (FIG. 5A), as measured by enzyme-linked immunosorbant assay (ELISA), and a histogram of anti-Tat antibody titers in the sera collected 4 to 6 months after the first injection (FIG. 5B). In FIG. 5A, sera were used at 1:500 dilution and antibody levels were expressed as optical density values (O.D.). Sera from nonimmunized study subjects did not exhibit detectable levels of Tat antibodies. A, B, C, D, and E represent immunized study subjects. In FIG. 5B, Tat antibodies were tested in sera at 1:1,000 to 1:64,000 dilutions and measured by ELISA. Titers are expressed as the highest dilution giving a positive reaction above threefold preimmunizing levels. Sera from nonimmunized individuals (controls: F and G) did not exhibit detectable titers of antibodies.

DETAILED DESCRIPTION OF THE INVENTION

To investigate whether particular serum markers in HIV infected individuals, such as antibodies against HIV-1 specificities or the p24 viral marker, are predictive of disease progression, serum was collected from 104 HIV-1 infected non-disease progressing individuals (chosen as individuals who have been infected more than eight years with CD4 cell counts always about 500 per mm$^3$ and with no clinical sign of disease) at the time of enrollment in the study and at follow-up one to two years later. At the follow-up, 26 of the HIV-1 infected individuals showed signs of disease progression (CD4 cell decrease over 30% or presence of clinical symptoms). In this study, the present inventors discovered that, of the serum markers tested (antibodies to HIV antigens including env, gag, nef and tat proteins, as well as p24 antigenemia, viremia, CD4 cell count and IFNα titer), anti-tat antibodies and p24 antigenemia were the best predictive markers in the serum, with the anti-tat antibodies being inversely correlated with p24 antigenemia, which is already known as a marker of viral replication. These were the only two serum markers that significantly correlated the two subgroups, infected individuals with serum marker level above the median and subjects with serum marker level below the median, with progression and non-progression of disease.

The serum levels of anti-tat antibodies and p24 protein are used as prognostic markers in prognostic methods and treatments in accordance with the present invention. By "prognosis", it is intended that the progressive state of the HIV infected individual in early infection can be predicted. Thus, as the serum levels of anti-tat antibodies correlate inversely with disease progression, at high serum levels of anti-tat antibodies, the HIV infected individual is in a state of non-progression. The serum level of anti-tat antibodies determines the progression state of an HIV infected individual. As long as the anti-tat antibody levels are still high, the individual is non-progressing. Once the level of anti-tat antibodies begins to drop, then the prognosis is that the infected individual is entering a progressive state.

While the serum level of anti-tat antibodies is the preferred prognostic marker, the serum level of tat protein can also be used as well (complexed or uncompleted). Like the correlation between anti-tat antibodies and p24 protein, the serum level of tat protein correlates inversely with anti-tat antibodies. The higher the serum level of anti-tat antibodies, the lower the serum level of tat protein, and, conversely, the lower the serum level of anti-tat antibodies, the higher the serum level of tat protein.

In addition, besides measuring the serum level of anti-tat antibodies or tat protein as a prognostic marker/indicator, the serum level of p24, which is already a known marker for viral replication, can also be used as a prognostic marker in the present invention because it has been discovered by the present inventors to be highly correlative with disease progression. Tests for p24 to diagnose HIV-1 infection (but not the progressive state of the individual) are commercially available.

The present invention is directed to a method for determining the prognosis of an HIV infected individual by measuring the serum level of one or more of anti-tat antibodies, tat protein, or p24 protein as prognostic markers, and comparing the measured level to levels of the prognostic marker indicative of disease progression or non-progression. It is further contemplated that the measurement of the level of one or more of the anti-tat antibody, tat protein or p24 protein prognostic markers can be combined with the measurement of other markers, such as viral load, CD4 cell count, or IFNα, to provide a more complete determination of the overall status of the HIV-1 infected individual. The level of any of the serum markers discussed above can be measured by any of a variety of assay techniques and is not limited to ELISA used in the Example herein, as would be appreciated by those of skill in the art. For instance these techniques could include the use of blots, beads, plates, immunoprecipitations, monoclonal or polyclonal antibodies against tat protein or fragments, the tat protein or tat peptides, competitive measurements or direct assays, enzymatic or radioactive markers, etc.

The correlation of high serum levels of anti-tat antibodies with non-disease progression among HIV infected individuals and low levels with disease progression strongly suggest that raising the serum level of anti-tat antibodies through active immunization may control viral replication. In this context, the present invention is also directed to a method for treating an HIV infected individual. The serum level of anti-tat antibodies is monitored over time in this method according to the present invention to determine whether the level of anti-tat antibodies has dropped sufficiently or the level of tat protein has increased sufficiently to warrant administration of a tat vaccine. By active immunization with a tat vaccine, the level of anti-tat antibodies is brought back up to a level indicative of non-disease progression. This same individual is monitored over time to confirm that the serum level of anti-tat antibodies is at a level predictive of non-disease progression and that this level is maintained over time. If a drop in serum level of anti-tat antibodies or an increase of tat protein in the serum is observed, further intervention, such as additional immunization with a tat vaccine, can be contemplated.

While the preferred tat vaccine is the tat toxoid vaccine disclosed in WO 96/27389, which contents are herein incorporated entirely by reference, the tat vaccine used in accordance with the present invention is not limited to such a tat toxoid vaccine. As will be appreciated by those skilled in the art, any tat vaccine which achieves the intended purpose of stimulating an immune response and raise the titer of anti-tat antibodies and which is within the skill of the art can be used in accordance with the present invention.

The present invention is further directed to a method for evaluating the immune response of a non-infected individual as the result of immunization with a tat vaccine. This method compares the level of anti-tat antibodies before and after immunization to determine the individual's humoral immune response to tat protein.

Having now generally described the invention, the same will be more readily understood through reference of the following examples, which are provided by way of illustration and is not intended to be limiting of the present invention.

EXAMPLE 1

Materials and Methods

Patients

Two groups of genetically homogeneous French Caucasians were recruited in various hospital centers in Paris and surrounding provinces in the context of the GRIV program (Hendel et al, 1996; Rappaport et al, 1997). The first group was composed of Non/Slow Progressors (NP) and consisted of 182 individuals enrolled on the basis of the following criteria: seropositivity for over 8 years (mean and median both 12 years); clinically asymptomatic in the absence of antiretroviral therapy; CD4 cell count never below 500/mm$^3$. These subjects represented approximately 1% of the seropositive individuals attending the hospital centers. In this group of asymptomatic NPs, 104 individuals had their follow-up available for a period of 1–2 years (mean and median 20 and 21 months) after their initial enrollment: clinical symptoms (CDC Stage B or C as defined by the 1993 classification) and laboratory parameters including CD4 cell count. Twenty-six of these 104 NPs showed signs of progression during 1 to 2 years of follow-up and were called Progressed Non-Progressors (NP-P), while the remaining 78 were called Non-Progressed Non-Progressors (NP—NP).

The second group was composed of 67 fast progressors (FP) defined as follows: seropositivity <3 years, treated with anti-HIV-1 drugs, clinically asymptomatic or not, and CD4 cell count below 300/mm$^3$. The FP population represented about 5% of the seropositive individuals recruited in clinics.

Upon enrollment in the GRIV study, cells and serum were shipped overnight to the laboratory of the present inventors and stored frozen. The present work was performed on this bank of sera collected at enrollment in the study.

Serological Tests

Sera from NP and FP patients, collected at the time of enrollment, and of healthy seronegative controls were investigated for the following serological parameters:

(1) The titer of antibodies to HIV-1 p24 protein and gag peptides, tat protein and tat peptides, nef protein, gp160 protein and gp120 peptides and tetanus toxoid (TT) was determined by standard ELISA, and results were expressed as OD of test serum subtracting the mean OD of control sera. The gag, env, tat, and nef proteins were prepared by recombinant engineering. The peptides tested were chemically synthesized (Neosystem, Strasbourg, France).

(2) Viral load in the serum was assessed using the *Virionquant kit* (Paris, France) which gives results as a number of eq copies/mm$^3$. Briefly, the viral RNA is extracted from the serum and used for RT-PCR with multiple pairs of HIV-1 primers. The amplified DNA product is then detected and quantitated using an ELISA system. The ODs are compared with those obtained for a standard, Virion-Standard™, covering 4 logs of eq copies/ml (from $10^2$ to $10^5$) and treated in parallel. The statistical analysis was performed on the log values.

(3) p24 antigenemia was measured by the HIV-1 p24 core profile ELISA kit (NEN-Dupont, cat# NEK060B) with the results expressed in pg/ml.

(4) IFNα Levels: The biological assay using VSV and MDBK cells was utilized to determine IFNα levels in serum, and the titers compared to the standard NIH ($2.5 \times 10^6$ IU/mg protein) were expressed in I.U.

Statistical Analysis

Statistical analyses were performed using SPSS for Windows, Ver. 7.5. Cumulative frequency distributions on each biologic parameter for all cases allowed for dichotomization of all continuous variables, in preparation for Chi-square analyses. Student T-tests were performed on each biologic parameter to compare means and standard deviations of values for NP—NP and NP-P groups. Pearson Correlations coefficients were computed to examine linear, one-to-one relationships for each pair of biologic parameters. Univariate linear regression analyses were conducted to examine the independent contribution of each covariate to the progression status (Table 5).

Multivariate regression analyses were performed to examine the relative behavior of each covariate in the presence all covariates in predicting progression.

Results

Tables 1 and 6 present data comparing NP and FP groups. Tables 2 to 5 present statistical comparisons of NP subjects on whom follow-up data were available (104 individuals): 78 of these NP cases were considered to be clinically stable (subgroup NP—NP); and 26 exhibited signs of progression towards AIDS during the follow-up (subgroup NP-P). Criteria, such as sex, age, as well as other HIV-1 antibody specificities, including gp160 and gp120 peptides (V3 loop and CD4 binding region), are not reported here because they do not exhibit any significant information.

Biological Characteristics Correlated to NP and FP Groups

Figure 1:
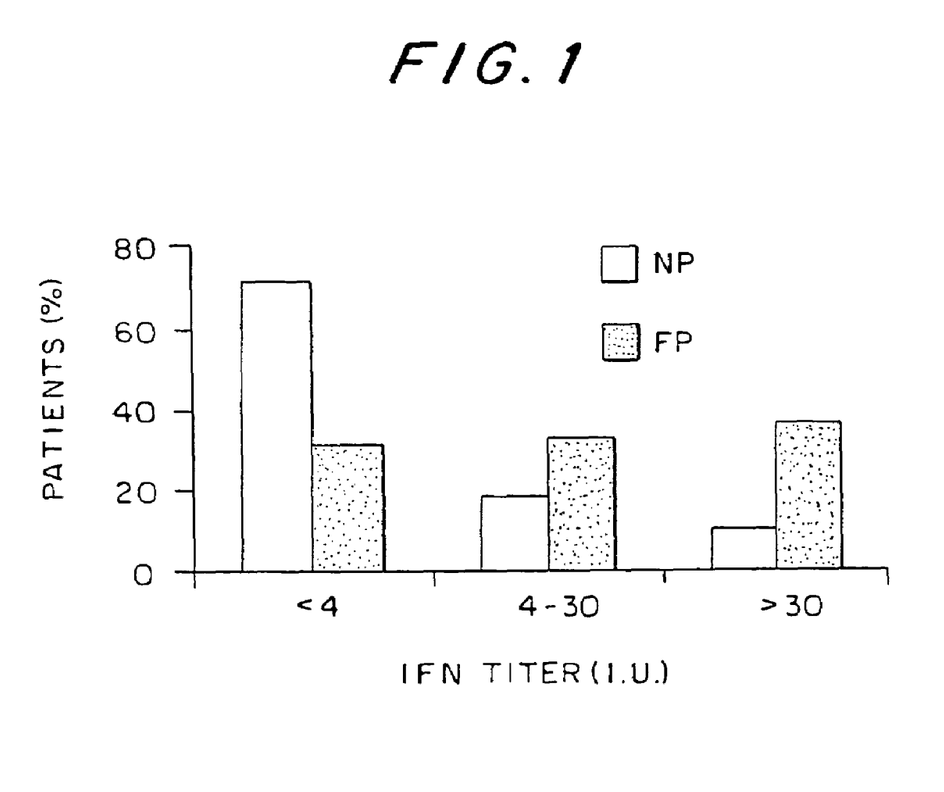
FIG. 1 shows a comparison of IFN$\alpha$ titers in sera from Non/Slow Progressor (NP), who are asymptomatic patients, and Fast Progressor (FP), who are sick patients. In the abscissa, IFN$\alpha$ titers are expressed as I.U. (<4, 4–30 and >30), and in the ordinate, percentages of patients NP (□) and FP (■).
Figure 2A:
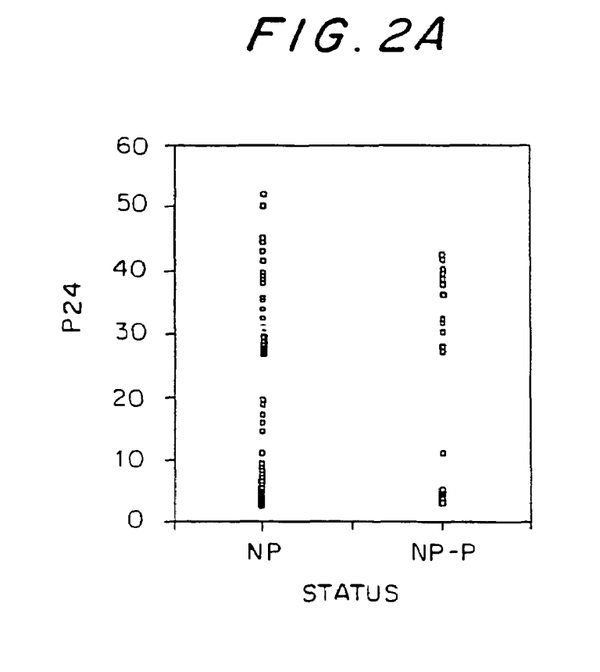
FIGS. 2A and 2B show pictorial representation of p24 OD distribution for NP and Progressed Non-Progressors (NP-P) subpopulations (FIG. 2A) and boxplot representation of the distribution (FIG. 2B). The dark boxes in the boxplots represent 75% of the distribution, the whiskers represent the upper and lower bounds of the outlier thresholds, above and below which are the outliers and the extremes.
Figure 2B:
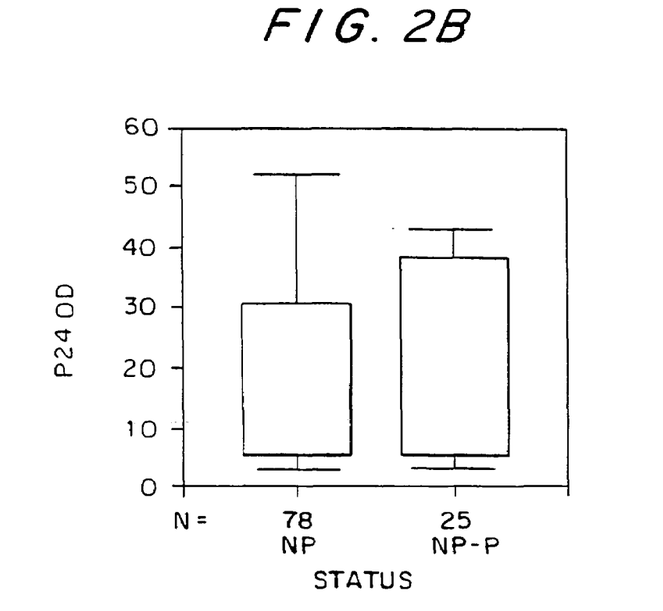
Figure 3A:
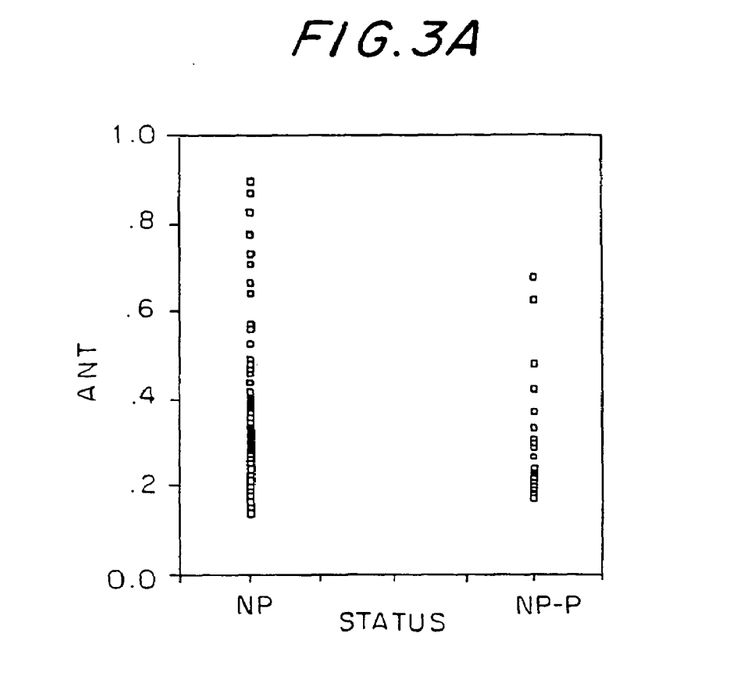
FIGS. 3A and 3B show pictorial representation of anti-tat Ab distribution for NP and NP-P subpopulations (FIG. 3A) and boxplot representation of the distribution (FIG. 3B). The dark boxes in the boxplots represent 75% of the distribution, the whiskers represent the upper and lower bounds of the outlier thresholds, above and below which are the outliers and the extremes.
Figure 3B:
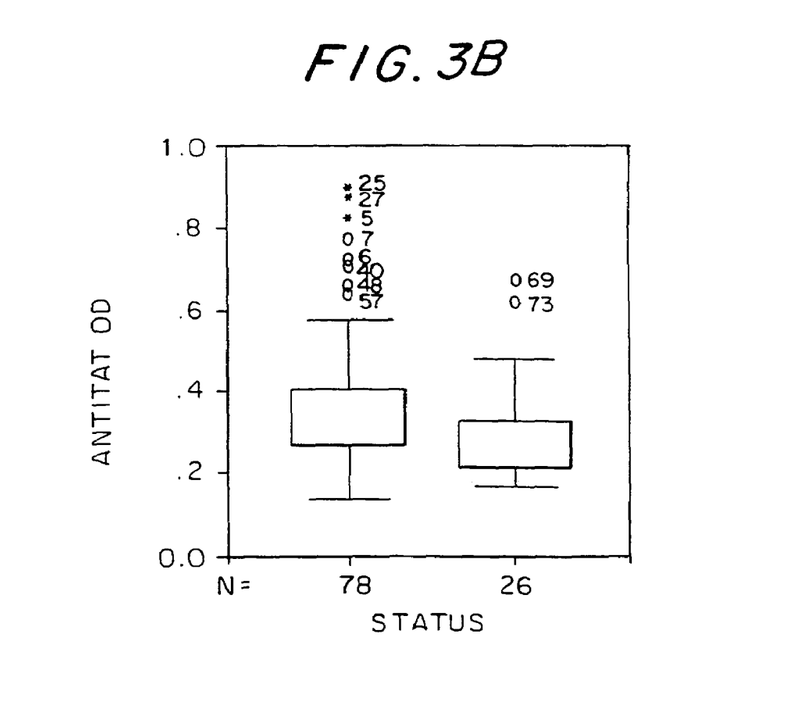
Figure 4A:
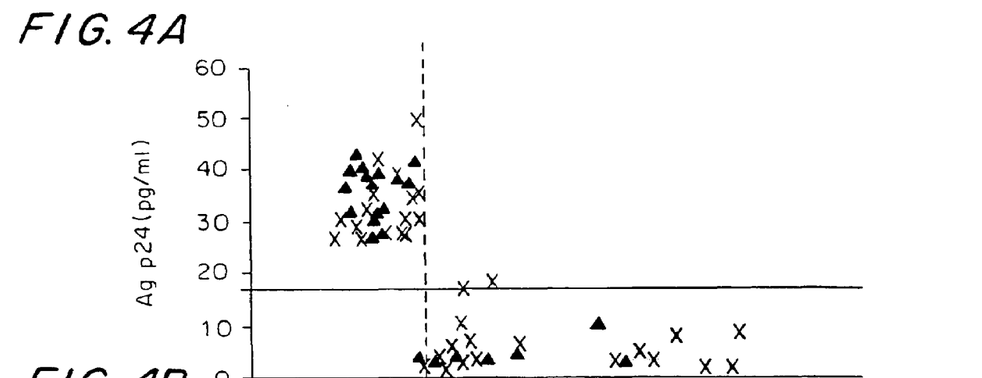
Figure 4B:
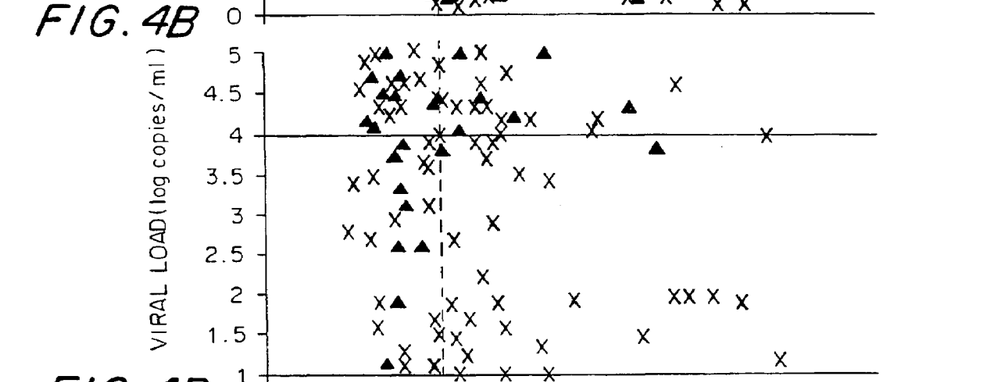
Figure 4D:
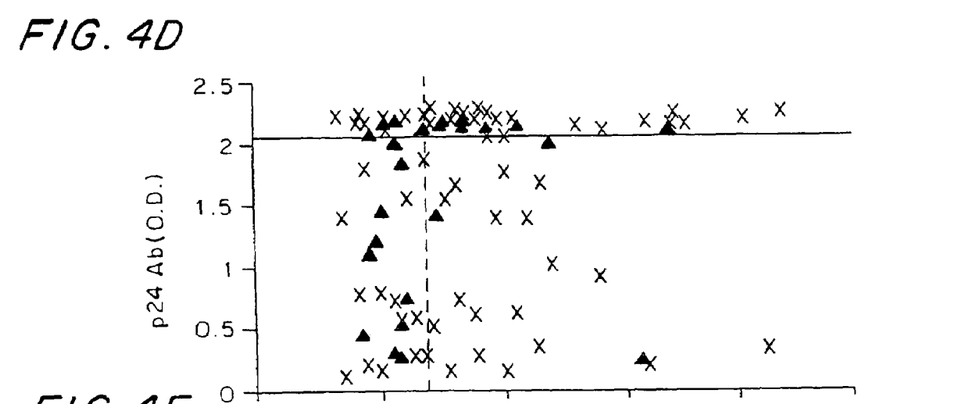
Figure 4E:
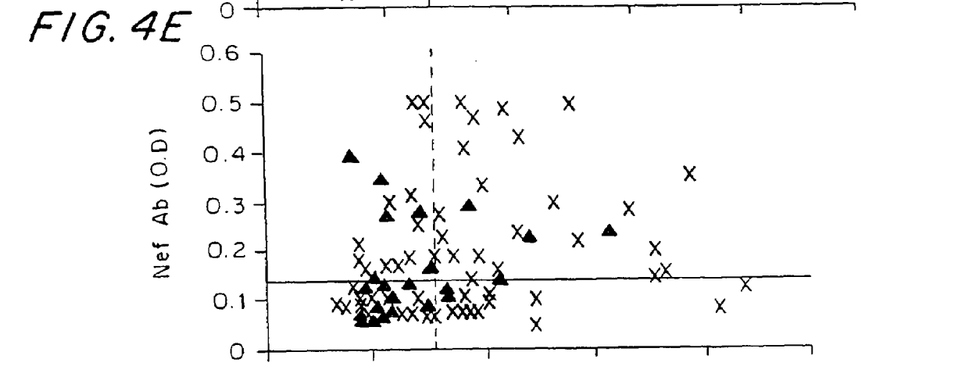
Figure 4F:
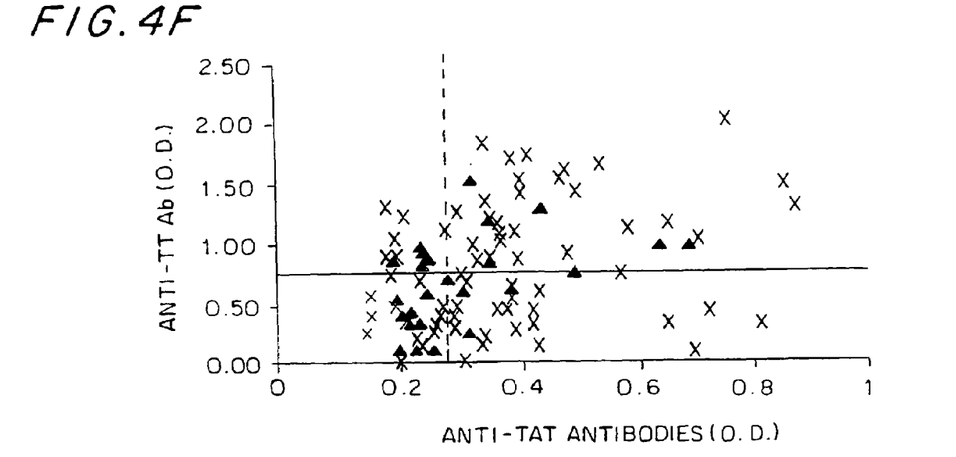

In addition to different predisposing genetic traits (Li et al, 1995; Westendorp et al, 1995), NP and FP populations of the GRIV cohort exhibited quantitative differences in serologic parameters (Table 1). In particular, the mean anti-p24 antibody level was significantly higher in the sera of NP individuals (p<0.0001) relative to the levels in sera from FP patients. The mean IFNα titers were significantly higher (p<0.0001) in the serum of FP than in those of NP. FIG. 1 shows the individuals with abnormal levels of serum IFNα. In addition, serum p24 antigen levels were significantly higher (p=0.004) and tat antibodies lower (p=0.03) in the FP group than in the NP group, but to a lesser extent than anti-p24 and IFNα. In contrast, the means of other tested parameters, including nef and TT antibody levels, were not significantly different in the two groups of patients (Table 1).

TABLE 1

T-test Comparisons of the Mean Biologic Parameters in the GRIV Cohort

| Biological Parameter | NP Mean (S.D.) N = 182 | FP Mean (S.D.) N = 67 | p-value (generated from Student T-test) |
|---|---|---|---|
| p24 antibody (O.D.) | 1.70 (0.72) | 0.56 (0.45) | p < 0.0001 |
| IFNα titer (IU) | 6.9 (13.6) | 22.6 (22.2) | p < 0.0001 |
| p24 ag (pg/ml) | 21.22 (16.4) | 29.55 (28.6) | p = .0046 |
| tat antibody (O.D.) | 0.39 (0.25) | 0.32 (0.17) | p = .032 |
| nef antibody (O.D.) | 0.22 (0.25) | 0.20 (0.26) | p = NS |
| TT antibody (O.D.) | 0.71 (0.45) | 0.82 (0.46) | p = NS |

NS = not significant

Biological Characteristics Associated with Progression of HIV-1 Infection in the NP Population Among the 104 NP patients for whom the follow-up was available since their enrollment, 26 subsequently exhibited a decline in CD4+ cell count below the initial value of greater than 30% or, alternatively, exhibited signs of clinical illness corresponding to CDC Stage B or C as defined by the 1993 classification. They were designated Progressed Non-Progressors (NP-P), while the remaining 78 stable individuals were designated Non-Progressed Non-Progressors (NP—NP).

Summary analyses were performed on each clinical and biologic parameter to explore their distribution and scatter. Once the ranges of values were found to be somewhat normally distributed and the means and medians determined, each parameter was divided into "High" and "Low" (or above and below their respective medians). Two-by-two tables were constructed using the Chi-square analysis procedure to test observed proportions against expected proportions within the NP and NP—P groups (Table 2).

TABLE 2

Chi-square Analyses of Biologic Parameters vs. Progression Status

| Biologic Parameter | Median Split | N of Cases NP-NP N = 78 | NP-P N = 26 | $X^2$ | p-value |
|---|---|---|---|---|---|
| Anti-TT | Low (0–.71) | 38 | 13 | 0 | .545 |
| | High (.72+) | 40 | 13 | | |
| Anti-tat | Low (0–.30) | 33 | 19 | 7.38 | .006 |
| | High (.31+) | 45 | 7 | | |
| Anti-nef | Low (0–.14) | 37 | 15 | 0.82 | .365 |
| | High (.15+) | 41 | 11 | | |
| Anti-p24 | Low (0–2.1) | 38 | 13 | 1.03 | .590 |
| | High (2.2+) | 38 | 13 | | |
| p24 ag | Low (0–19) | 44 | 8 | 5.12 | 0.20 |
| | High (20+) | 34 | 18 | | |
| Viral Load | Low (0–3.9) | 41 | 10 | 2.01 | .141 |
| | High (4.0+) | 36 | 16 | | |
| CD4 | Low (0–710) | 34 | 17 | 3.10 | 0.78 |
| | High (711+) | 41 | 9 | | |

NP-NP are stable Non-Progressors while NP-P are the Non-Progressors who have progressed during the follow-up. "High" and "low" groups were determined by dichotomizing all cases by the median split for each biologic parameter.

Among the biological parameters tested, the most discriminative for stability versus progression was anti-tat antibodies (p=0.006), followed by p24 antigenemia (p=0.020). CD4 cell counts (p=0.078) and viral load (p=0.141) were not as impressive in their ability to discriminate between these progression categories. As shown in the subgroup of NP exhibiting higher CD4+ cell counts, there were fewer cases with signs of progression than there were in cases with lower CD4 cells counts (18% versus 33%), but this relationship was not statistically validated. Although the viral load was low in most NP patients (<$10^4$ copies/ml), those who later progressed toward AIDS had relatively higher levels of serum viral RNA (31% versus 19%), but this disparity did not achieve statistical significance. No difference between the two groups was found with other antibody specificities including p24, nef and TT.

As seen in Table 3, Pearson correlation analyses were conducted on all 104 NP patients to examine the one-to-one relationships of each pair of continuous biological parameters, and were followed by analyses for each disease-progression category. Anti-tat and p24 (both measured in O.D.) were very highly and inversely correlated (r=−0.641, p=0.000). Interestingly, anti-TT levels were moderately correlated with anti-tat levels (r=0.341, p=0.000). Pearson correlations were also performed within each disease-progression category resulting in very much the same associations; however, no significant correlation was found between viral load and anti-p24, and viral load and anti-TT in the NP-P group.

TABLE 3

Pearson Correlations of Biologic Parameters for All Cases, and Then by Disease Progression Status

| Correlation Pair | | All Cases n = 104 r (p value) | Status = NP n= 78 r (p value) | Status = NP-P n= 26 r (p value) |
|---|---|---|---|---|
| Anti-tat | Anti-TT | .341 (.000) | .310 (.006) | .443 (.024) |
| Anti-tat | p24 | −.641 (.000) | −.602 (.000) | −.732 (.000) |
| p24 | Anti-p24 | −.238 (.016) | −.226 (.050) | −.352 (NS) |
| p24 | Anti-TT | −.335 (.001) | −.253 (.025) | −.623 (.001) |
| VL | Anti-tat | −.176 (NS) | −.202 (NS) | .291 (NS) |
| VL | Anti-p24 | −.204 (.040) | −.272 (.018) | .008 (NS) |
| VL | Anti-TT | −.217 (.028) | −.229 (.045) | −.052 (NS) |

In the NP-P patients, for whom levels of p24 antigenemia were higher than in the NP group (Table 2), tat antibody levels were inversely correlated to p24 antigenemia (r=−0.732, p<0.001) (Table 3). Furthermore, most of the NP-P patients who are at advanced stages of infection exhibited AIDS-related clinical manifestations, despite anti-retroviral therapy. Of the few remaining asymptomatic individuals (20%), the majority belonged to the NP-P subgroup with high tat antibodies (>0.31 O.D.)

Univariate and multivariate analyses of biologic factors and their value in predicting progression status were then performed. When each covariate was examined as a univariate predictor of disease progression (Table 4), anti-tat, p24 and viral load significantly predicted progression status. However, none of these independent relationships reflect the multiplicity of factors acting in consonance to produce disease progression.

TABLE 4

Univariate Analysis of Covariates as Predictors of Disease Progression

| Independent Covariate | β | p-value |
|---|---|---|
| Anti-nef | −.101 | .309 |
| Anti-p24 | .049 | .625 |
| Anti-tat | −.208 | .035 |
| Anti-TT | −.092 | .351 |
| p24 | .225 | .022 |
| VL | .216 | .028 |

A more practical approach, perhaps, to this exploration of interactions among biologic parameters is the multivariate approach. Four methods of stepwise multiple regression were performed to examine the influence of each covariate on disease progression in the presence of all others (Table 5).

TABLE 5

Backward Elimination of Covariates from a Multiple Regression Model to Predict Disease Progression

| Model | | Unstandardized Coefficients | | Standardized Coefficients | | |
|---|---|---|---|---|---|---|
| | | β | Std. Error | of β | t | Sig. |
| 1 | (Constant) | .495 | .590 | | .840 | .403 |
| | Anti-nef | −.187 | .309 | −.061 | −.607 | .545 |
| | Anti-p24 | .186 | .116 | .155 | 1.605 | .112 |
| | Anti-tat | −.212 | .707 | −0.39 | −.300 | .765 |
| | Anti-TT | 7.305E-02 | .205 | .038 | .357 | .722 |
| | p24 | 1.320E-02 | .008 | .229 | 1.711 | .090 |
| | VL | .149 | .073 | .211 | 2.042 | .044 |
| 2 | (Constant) | .387 | .463 | | .835 | .406 |
| | Anti-nef | −.200 | .304 | −.065 | −.659 | .512 |
| | Anti-p24 | .190 | .115 | .169 | 1.652 | .102 |
| | Anti-TT | 6.738E-02 | .203 | .035 | .332 | .740 |
| | p24 | 1.461E-02 | .006 | .253 | 2.399 | .018 |
| | VL | .151 | .072 | .214 | 2.093 | .039 |
| 3 | (Constant) | .474 | .381 | | 1.243 | .217 |
| | Anti-nef | −.205 | .303 | −.067 | −.678 | .499 |
| | Anti-p24 | .186 | .114 | .166 | 1.637 | .105 |
| | p24 | 1.3955-02 | .006 | .242 | 2.432 | .017 |
| | VL | .145 | .070 | .207 | 2.077 | .040 |
| 4 | (Constant) | .406 | .367 | | 1.106 | .272 |
| | Anti-p24 | .179 | .113 | .159 | 1.582 | .117 |
| | p24 | 1.416E-02 | .006 | .246 | 2.483 | .015 |
| | VL | .154 | .069 | .218 | 2.228 | .028 |
| 5 | (Constant) | .804 | .268 | | 2.996 | .003 |
| | p24 | 1.203E-02 | .006 | .209 | 2.153 | .034 |
| | VL | .133 | .069 | .189 | 1.948 | .054 |

[a]Dependent Variable: STATUS

The most informative entry method of covariates is the backward elimination model which removes covariates in order of increasing predictive value on progression status. All continuous covariates were entered into the equation to predict progression status (1=Stable NP, 2=Progressed NP). Curiously, the first covariate to be removed from the model was anti-tat, followed by anti-TT, anti-nef, then anti-p24, leaving Viral Load (β=0.133, p=0.054) and p24 (β=0.012, p=0.034) as the most important predictors of the disease progression status.

Each covariate was divided into two groups (high or low) by the respective median of the distribution. These dichotomized covariates were then entered into a multivariate regression to measure their independent contributions in predicting disease status; a surprising reversal of covariate removals was observed, which indicates that p24 (which one would expect to be the most important predictor of disease status) was removed first, indicating that it had the least predictive effect on disease progression, followed by anti-nef, anti-TT, anti-p24, viral load, leaving anti-tat as the most prominent predictor of disease progression (β=−0.465, p=0.007). The discordance of results from one method to another leads one to seriously consider the implications of making analytic decisions about making important grouping decisions for continuous biologic parameters (i.e., dichotomizing covariates before entry into a complex system).

FIGS. 2A–2B and FIGS. 3A–3B illustrate the overall means and scatter of the p24 and the anti-tat values as measured by optical density for the NP—NP and NP-P groups.

Relationships Between tat Antibody Levels and Other Parameters

In the 182 NP enrolled in the cohort, tat antibody levels were compared with the other biological parameters to investigate the mechanisms leading to the strong correlation between high tat antibody levels and clinical stability. FIGS. 4A–4F show that in the NP subgroup with high tat antibody levels (>0.31 O.D.; i.e., above the median), fewer subjects exhibited signs of progression than in the subgroup with low tat antibody levels (<0.31 O.D.; i.e., below the median). These differences are highly significant (Table 6).

TABLE 6

T-test Comparison between High and Low anti-tat Responders for Biological Parameters in NP and Subjects Mean (SD)

| | NP | | | FP | | |
|---|---|---|---|---|---|---|
| | tat high* | tat low | p | tat high* | tat low | p |
| p24 ag (pg/ml) | 8.03 (7.4) | 35 (10.9) | <.001 | 7.03 (29.2) | 9.97 (23.8) | <.001 |
| p24 antibody (O.D.) | 1.77 (0.7) | 1.64 (0.73) | NS | 0.43 (0.38) | 0.66 (0.64) | NS |
| CD4 cells/ml | 793 (295) | 819 (333) | NS | 365 (276) | 326 (223) | NS |
| Lot[10] Viral Load (eq. RNA copies/ml) | 3.36 (1.19) | 3.52 (1.18) | NS | ND | ND | — |

ND = Not Determined
NS = Not significant
For each parameter, patients were distributed into two groups based on tat antibody levels which were high (above the median) and low (below the median).

In Table 6 the subgroups of NP with high and low tat antibody levels were compared with the T test for clinical and laboratory parameters (CD4[+] cell counts, p24 antigen, p24 antibody, and viral load). P24 antibodies, viral load, and CD4 did not discriminate significantly between NPs with low and high tat antibody levels while p24 antigenemia did. The same result was found comparing FPs with low and high tat antibody levels.

Discussion

The GRIV project was initiated to investigate genetic and immunologic parameters which determine the disparate courses of disease progression in various HIV-1 infected individuals ranging from 2 to greater than 17 years. To perform the study, two groups of genetically well-defined seropositive subjects were selected, one group was composed of healthy asymptomatic subjects infected for 8 years (NP), and the other group was composed of patients at advanced stages although infected more recently (<3 years) (FP) recruited in different hospital centers in France. The selection criteria used to include subjects in either of these two extreme groups of patients were such that NP represents about 1% and FP approximately 3% of the total seropositive patients being followed in the centers.

In the present study, immunological and virological serum parameters were evaluated to determine those parameters contributing to establish the course of HIV-1 disease progression, fast versus non/slow-progression. Furthermore, among the NP group, the cellular and serum blood factors associated with the progression of HIV-1 disease in those individuals who were initially asymptomatic at enrollment were investigated.

The NP status, as opposed to the FP one, was chiefly correlated to the p24 antibody, and inversely correlated to circulating IFNα titers. Among Non/Slow Progressors (NP), the subsequent progression toward AIDS, as determined by clinical and/or biological symptoms, was chiefly associated with low tat antibody levels and high p24 antigen. Of interest, high antibody levels to tat peptide (AA1-15) but not to other regions of the protein were also correlated to stability (not shown).

The high inverse correlation found between anti-tat antibodies and p24 antigenemia in all subjects gives a unique status to the tat protein compared to the other HIV-1 proteins investigated in this study, namely gp120, nef and p24. Because progression of the disease in asymptomatic HIV-1 infected individuals (NP subjects at enrollment) appears to be very much associated (p=0.006) with low anti-tat antibodies (<0.31 O.D.), anti-tat antibodies are a critical marker of initiation of immune dysfunction (disease progression) in advance of p24 antigenemia, which reflects viral replication activity.

Antibodies to tat recognize tat protein in the extracellular milieu but not within HIV-1 infected cells. Thus, the anti-tat effect of these specific antibodies prevents this viral protein from targeting uninfected cells including immune cells (Viscidi et al, 1989; Chirmule et al, 1995). In this context, tat antibodies could contribute to locally prevent the tat-induced cellular immune suppression in those lymphoid foci with acute infection and extracellular tat, as they do in vitro in activated PBMC infected by HIV-1 (Zagury et al, 1998a). Anti-tat antibodies may neutralize the capacity of tat to inhibit the immune response to recall antigens, to prime non-infected T cells for activation-induced apoptosis, and, further, to prime non-infected cells for infection by HIV-1 (Li et al, 1995). Thus anti-tat antibodies may control in vivo HIV-1 replication indirectly by preventing tat-mediated immune suppression and programmed death of activated immune cells.

It has been previously demonstrated that the CTL response is initially effective in controlling HIV-1 infection, and the loss of this response is associated with progression of HIV-1 infection toward AIDS (Borrow et al, 1997; Goulder et al, 1997). The role of CD8 cells in mediating control of HIV-1 infection may be through direct cytolysis of HIV-1 infected cells and/or by release of soluble factors (i.e., C—C chemokines) within the context of the cellular immune response. CD8+ cells from multiply exposed, but non-infected, individuals have been demonstrated to confer protective immunity to hu-PBL-SCID mice challenged with HIV-1 infection (Zhang et al, 1996).

tat-induced loss of cellular immune reaction, particularly the absence of effector CTLs, appears to be accompanied by decrease of anti HIV-1 C—C chemokines (Zagury et al, 1998a). As a consequence, loss of control of virus replication ensues in infected patients (Borrow et al, 1997; Goulder et al, 1997; Zagury 1997). Circulating tat antibodies may exert a protective role by blocking the tat-induced suppressive effect on the cellular immune response to infected cells, as well as other opportunistic pathogens, resulting in the control of viral replication and maintenance of immune functions. The control of viral replication by tat antibodies is highly suggestive by the inverse correlation (p<0.001) found in the GRIV cohort between tat antibodies and p24 antigenemia (Table 3 and FIG. 4A).

These studies showing that tat antibodies correlate with non-progression and previous in vitro results demonstrating the role of extracellular tat in suppressing T cell response to antigen including C—C chemokine production (Zagury et al, 1998a) and CTL activation (Zagury et al, 1997), in promoting activation induced T cell apoptosis and priming non-infected cells for virus replication (Li et al, 1997), prompted the present inventors to establish a new strategy based on anti-tat active immunization (Gringeri et al, submitted). The present study provides a strong rationale to include tat immunogen as an integral AIDS vaccine component in order to permit sustained cellular immune responses in the face of the immunopathologic effects of HIV-1 infection. Toward this end, a strategy for tat preparation, namely tat-Toxoid was developed (Gringeri et al, submitted). This strategy should permit successful application of conventional vaccine strategies using anti-HIV-1 CTL-inducing antigens (Picard et al, 1992; Achow et al, 1990; Nixon et al, 1991). tat immunization may be an effective strategy to circumvent tat-induced immune suppression and viral dissemination. In the absence of these effects, the immune system may be capable of responding successfully in response to HIV-1 infection. Thus the tat-Toxoid approach may be an essential component of therapeutic as well as preventive vaccine strategies against AIDS.

Example 2

Materials and Methods

Subjects

Fourteen HIV-1-infected but asymptomatic patients volunteered to participate in this open phase I pilot study and signed the local Ethics Committee-approved informed consent.

Of 14 anti-HIV-positive asymptomatic patients enrolled in the study, 11 were men with hemophilia aged 19 to 39 years (median, 31 years). The remaining 3 patients were women aged 20 to 36 years (median, 33 years) who had been infected by heterosexual contacts. The duration of HIV-1 infection ranged from 4 to 15 years (median, 12 years). Eight of 14 patients had never received antiretroviral treatment, whereas the remaining 6 had been on antiretroviral treatment for at least 1 year. Among these 6 patients, 4 had been treated with three drugs, including proteinase inhibitors, for at least 6 months. Furthermore, 6 of 14 enrolled patients had been previously anti-IFN-α immunized, of whom 3 were receiving antiretroviral treatment.

CD4+ cell counts ranged from 219 to 453 cells/mm$^3$ (mean±SD 293±70 cells/mm$^3$) at the time of enrollment. Other immunologic and virologic parameters are shown in Table 8. All 11 hemophiles were also infected with hepatitis C virus (HCV).

Immunization

Immunogen

TAT toxoid was prepared by chemical inactivation of recombinant HIV-1 TAT protein purified by solubilization in 6M guanidine and HCl-containing buffer followed by chromatography on nickel agarose (NTA, Quiagen, Hilden, Germany). The protein was expressed in *Escherichia coli* as a fusion protein in pRSETA (Invitrogen, San Diego, Calif., U.S.A.) and contained six hystidine residues (i.e., a nickel-binding site). HIV-1 TAT cDNA expression vectors were derived from HIV-1-MB, pCV1. Purified TAT protein, but not TAT toxoid, exhibited strong biologic activity as measured by the CAT assay on HeLa cells. The activity of native TAT was inhibited by murine anti-TAT Ab.

HIV-1-TAT toxoid was manufactured by Bio Sidus (Buenos Aires, Argentina) under Good Laboratory Practice conditions.

HIV-1 Tat Immunizing Preparations

Priming preparation: 100 µg of HIV-1 TAT toxoid in water-in-oil emulsion (incomplete Freund adjuvant HFA with Seppic mineral oil, ISA051).

Booster preparation 50 µg of HIV-1 TAT toxoid in water-in-oil emulsion HFA, Seppic ISA051).

Immunization Schedule

HIV-1-seropositive subjects were intramuscularly injected with HIV-1 Tat priming preparation and boosted every 1 to 2 weeks (immunization A) or every 4 weeks (immunization B) until a twofold or greater rise of the preimmunization level of anti-Tat Abs, determined in optical density (OD), was detected by enzyme-linked immunosorbent assay (ELISA) in the sera collected 7 to 14 days after each injection. Subsequently, the anti-Tat immunization was maintained by boosting with Tat every 3 to 4 months according to the anti-TAT Ab levels. Schedule A included 8 patients and schedule B included 6 patients.

Tolerance Evaluation

Safety and tolerance were assessed by clinical examination, patient symptoms, and laboratory evaluation (biochemistry and complete blood cell counts). Local and systemic side effects were recorded 7 days after each injection.

Safety Evaluation

Signs and symptoms related to AIDS progression were carefully looked for over the follow-up period by clinical examination. Any change in antiretrovial treatment was noted.

CD4$^+$ cell counts (PACS with Ortho Diagnostics monoclonal antibodies, Raritan, N.J., U.S.A.), HIV-1 plasma viremia (RNA PCR, ELISA kit from Viroquant, Paris, France) and HIV-1-p24 antigenemia (ELISA, NEN-Du Pont, Nemours, France) were the main parameters followed for evaluation of safety. The Viroquant ELISA kit for HIV-1 RNA has a sensitivity threshold of 10 cq copies/mL. The ELISA kit for p24 antigenemia has a sensitivity threshold of 4.4 pg/mL. In addition, liver function tests were accurately monitored in HCV-positive patients.

Immunogenicity Evaluation

Immunogenicity-of-TAT toxoid was evaluated by assaying anti-HIV-1 TAT Abs by ELISA 7 to 14 days after each injection. The serum anti-Tat Abs were detected by standard ELISA assay using flat-bottomed, 96-well Costar plates (Costar, Cambridge, Mass., U.S.A.). Tat recombinant protein was fixed on the plate at 50 ng/well. Sera at 1:500 dilution were tested according to the standard ELISA procedure, and the results were expressed as OD values. Circulating Tat Ab levels varied among infected patients. In contrast, in all infected but not immunized patients (>100 subjects tested), consecutive serum samples collected within a 1-year period and tested in the same experiment under the same ELISA condition do not exhibit variability in their Tat Ab levels less than ±1.5-fold). This is the reason why responders were defined as those patients showing an increase in anti-HIV-1 TAT Ab levels of twofold or more from preimmunization values. Cell-mediated immunity (CMI) and delayed-type hypersensitivity (DTH) response toward HIV-1-TAT protein were evaluated at random by lymphoproliferative response and skin tests, respectively. CMI was assayed by T-cell proliferation measured by $^3$H-thymidine incorporation; fresh peripheral blood mononuclear cells (PBMCs) from patients were cultured for 6 days in 96 well round-bottomed culture plates in the presence (test samples) or absence (control samples) of 10 µg/mL of Tat toxoid. Eighteen hours before the completion of the culture, 0.5 µCi of thymidine was added to each well. Cells were then harvested, and thymidine incorporation in cell DNA was measured in a β counter and expressed as counts per minute (cpm) per milliliter. Results are expressed as the ratio or cpm in test samples to cpm in control samples, and a ratio of >2 was considered as positive (Picard et al., 1992). Administration of an intradermal injection of Tat toxoid (10 mg) in 100 mL phosphate-buffered saline (PBS) was carried out for the DTH skin test. Positive skin tests corresponded to a papula of >1 cm diameter measured at 48 hours.

Six nonimmunized HIV-1-seropositive and 6 sero-negative subjects matched for age, gender, and CD4$^+$ cell counts (the latter only in HIV-seropositive patients) were used as controls for these tests.

Results

Safety and Tolerance

Seven of 14 patients entered in the study reported mild fever (up to 38° C.) lasting 12 to 48 hours after the first injection (priming preparation). Nine of 14 patients complained of pain and swelling at the site of the first injection (priming preparation) requiring anti-inflammatory drugs. Pain and swelling resolved 2 to 7 days after the injection in all cases. No side effects were reported on successive injections.

Clinical evaluation showed no signs of HIV-1 disease progression and no concomitant diseases related or unrelated to HIV-1 infection. Antiretroviral treatment did not have to be changed during immunization and follow-up in any patients.

Absolute CD4$^+$ cell counts increased significantly after immunization, with a mean difference from preimmunization values of 60 cells/mm$^3$ (95% confidence interval, 34–85 cells/mm$^3$; Student's t-test for paired samples, t=4.99; P=0.0002), whereas the CD4$^+$ cell percentage did not change significantly (Table 7).

Up to the last follow-up visit, HIV-1 plasma viremia did not significantly change after immunization from preimmunization levels, although a trend toward a decrease was observed (mean difference from preimmunization values, −0.63 eq RNA copies×10 mL; 95% confidence interval, −1.341 to +0.067 eq RNA copies×10$^4$ mL; Student's t-test for paired samples, t-1.95; P=0.0725); baseline and follow-up levels are shown in Table 7.

HIV-1 p24 antigenemia did not change significantly after immunization from preimmunization levels of Student's t-test for paired samples, t=1.76, P=0.10), even though 4 of 14 patients showed a decrease (Table 7). Liver function tests as well as other biochemical or hematologic parameters did not show any difference from preimmunization values.

TABLE 7

Absolute CD4* Cell Counts HIV-1 Plasma Viremia, and Antigenemia in 14 HIV-1-Seropositive Patients Immunized With Inactivated Recombinant HIV-1 TAT Preparation

| | | CD4* Cell Counts/mm³ (%) | | HIV-1 Plasma Viremia$^\alpha$ | | HIV-Ag (pg/mL) | |
|---|---|---|---|---|---|---|---|
| Code | Follow-Up (months) | Preimmunization | At End of Follow-UP | Preimmunization | At End of Follow-UP | Preimmunization | At End of Follow-UP |
| 1 | 8 | 284 (28.4%) | 345 (34.5%) | 5.75 | 5.71 | 11 | 4 |
| 2 | 8 | 453 (16.8%) | 534 (18.4%) | 2.06 | 2.15 | 32 | 3 |
| 3 | 12 | 227 (28.4%) | 345 (34.5%) | 0.35 | <0.001 | 17 | 4 |
| 4 | 3 | 287 (22.1%) | 252 (21.0%) | 0.49 | 0.70 | 3 | 3 |
| 5 | 5 | 282 (28.2%) | 319 (22.8%) | 3.34 | 0.91 | 4 | 4 |
| 6 | 9 | 224 (11.8%) | 294 (12.8%) | 5.23 | 3.90 | 3 | 3 |
| 7 | 3 | 313 (24.1%) | 443 (23.3%) | 5.39 | 5.55 | 4 | 4 |
| 8 | 4 | 275 (30.6%) | 314 (31.4%) | 4.12 | 3.18 | 5 | 4 |
| 9 | 6 | 274 (8.3%) | 386 (9.9%) | 5.08 | 5.74 | 4 | 5 |
| 10 | 8 | 295 (22.7%) | 372 (26.6%) | 4.02 | 3.9 | 5 | 4 |
| 11 | 4 | 219 (16.9%) | 235 (23.5%) | 4.01 | <1 | 8 | 3 |
| 12 | 12 | 272 (20.9%) | 340 (30.9%) | 4.74 | 2.30 | NA | 4 |
| 13 | 9 | 435 (33.5%) | 478 (28.1%) | 4.30 | 4.07 | 3 | 4 |
| 14 | 3 | 257 (13.5%) | 274 (13.7%) | 2.05 | 2.90 | 3 | 3 |

$^\alpha$HIV-1 plasma viremia is measured in equivalent copies 10,000/ml (see methods)
NA — not available Immunogenicity Eight patients were assigned to induction schedule type A on a voluntary basis and the remaining 6 patients followed immunization scheme B. All patients responded to TAT immunization with an increase in Abs to Tat ranging from twofold to eightfold (Table 8), including patients who were treated with antiretroviral drugs, immunized against IFN-α or both. Patients received 1 to 8 injections to induce and maintain an Ab response during a follow-up period of 3 to 12 months (median, 8.5 months). An Ab response defined as a twofold or more rise of anti-HIV-1 TAT Ab level from preimmunization levels, was achieved with 1 to 5 injections (median, 3 injections) both in patients with induction type A (injection every 1–2 weeks) or type B (injections every 4 weeks).

Four of 8 tested patients showed a positive DTH response to intradermal injection of inactivated recombinant TAT protein with persistence of skin induration (papula) up to 72 hours (Table 8).

TABLE 8

Immunogenicity of Anti-HIV-1 TaT Toxoid in HIV-1-Seropositive Patients
Anti-TAT Antibody level (OD)

| Code | Immunization Type (A/B) | Preimmunization | Peak | DTH Response | CMI Response |
|---|---|---|---|---|---|
| 1 | B | 0.240 | 1.230 | NA | NA |
| 2 | A | 0.104 | 1.526 | NA | Positive |
| 3 | B | 0.217 | 0.537 | Negative | Negative |
| 4 | B | 0.214 | 1.063 | Positive | NA |
| 5 | A | 0.446 | 1.612 | NA | NA |
| 6 | A | 0.213 | 0.664 | Negative | Negative |
| 7 | A | 0.204 | 1.139 | NA | NA |
| 8 | B | 0.104 | 1.045 | Positive | Positive |
| 9 | A | 0.422 | 0.812 | Negative | NA |
| 10 | B | 0.125 | 1.492 | NA | NA |
| 11 | A | 0.252 | 0.682 | Negative | NA |
| 12 | A | 0.410 | 2.219 | Positive | Positive |
| 13 | A | 0.162 | 0.508 | Positive | Positive |
| 14 | B | 0.120 | 2.012 | NA | NA |

DTH delayed-type hypersensitivity:
GMI, cell-mediated immunity:
NA, not assayed:
OD, optical density.

Four of 6 patients showed a consistent increase of proliferative response to the Tat antigen in assays of CMI (Table 8) that was twofold to 10-fold compared with cells cultured without any antigens. In 3 positive patients (P3, P8, and P12), frozen PBMCs collected prior to Tat immunization were available. T-cell proliferation of these cells following Tat toxoid stimulation did not yield any positive proliferative response (data not shown). Thus, Table 8 shows the use of ELISA anti-Tat to monitor the patients and show that the titer of the patients for anti-Tat antibodies has increased following immunization. This demonstrates that the measure of anti-Tat antibodies is a good test to follow-up patients and provide a prognosis of disease evolution.

None of the HIV-1-seropositive or seronegative control subjects exhibited an increase of anti-TAT Ab levels and CMI response to Tat protein. Non of the controls showed a positive response to DTH skin test to Tat protein.

Discussion

This pilot phase I study was designed to demonstrate safety, tolerance, and immunogencity of a preparation of HIV-1 TAT toxoid in immunocompromised HIV-1-seropositive patients, even those concurrently treated with antiretroviral drugs, immunized against IFN-α or both.

This study showed that anti-HIV-1 TAT immunization in these patients was safe and well tolerated. Biochemical, hematologic, immunologic, and virologic parameters as well as clinical evaluation did not suggest any toxic effect of immunization. Moreover, absolute CD4⁺ cell counts appeared to increase after immunization in most of patients, and in some patients, a decrease in HIV-1 plasma viremia and p24 antigenemia occurred. Additionally, none of the immunized patients showed an increase in virologic parameters during the follow-up period, even though many were not given antiretroviral drugs. These results are consistent with the protective role of anti-TAT Abs, (Lolli et al., 1995; Krone et al., 1988; and Reiss et al., 1991) correlated inversely with p24 antigenemia and illustrated in nonprogressor patients (Zagury et al., 1998).

This study showed that the immunizing preparation of HIV-1 TAT toxoid was highly immunogenic; all patients who were at different degrees of HIV-1-related immunodeficiency responded and some did so after just one injection. Immunization induced CMI, a positive cell-mediated immunity, and even a DTH response in at least some of the patients evaluated.

It should be stressed that this active immunization aiming at reducing the TAT toxin pathogenic effects (Viscidi et al., 1989; Chirmule et al., 1995 and Zagury et al., 1996), can be used in combination with antiretroviral treatments, anti-IFN-α immunization, or both. It will be important to expand the observations derived from this pilot phase I study in a larger group of patients.

Because extracellular TAT can be considered an HIV-1 strategy to induce immune suppression and apoptosis on nonifected immune cells (Viscidi et al., 1989; Chirmule et al., 1995 and Zagury et al., 1996), we propose to counteract these deleterious effects by an anti-Tat immunization. Tat toxoid could be an integral vaccine component for seronegative (preventive) or seropositive (therapeutic) people. Such a vaccine preparation comprising HIV-1 CTL-inducing epitopes should combat cellular immune suppression, (Zagury et al., 1998) viral replication (Zagury et al., 1998) and natural progression toward AIDS, (Goulder et al., 1996; Borrow et al., 1997 and Zagury, 1997) if not viral entry.

Example 3

Methods and Materials

The open, controlled, phase I vaccine trial was designed to evaluate safety and immunogencity of a Tat toxoid preparation (Gringeri et al., 1998) in 5 seronegative study subjects, over a 6-month follow-up period.

Immunizing Reagents

The immunogen referred to as Tat toxoid was a chemically inactivated recombinant HIV-1 Tat protein (Le Buanee et al., 1998; and Gringeri et al., 1998) adjuvanted with incomplete Freund adjuvant (IFA), which consisted of the mineral of ISA 051 from Seppic (Paris, France). TAT toxoid was prepared by chemical inactivation of recombinant HIV-1 TAT protein purified by solubilization in 6 M guanidine. HCl-containing buffer, followed by chromatography on nickel agarose (NTA, Qiagen, Hilden, Germany). The protein was expressed in *Escherichia coli* as a fusion protein in PRSETA (Invitrogen, San Diego, Calif., U.S.A.) that contained six hystrix residues (nickel binding site). HIV-1 TAT cDNA expression vectors were derived from HIV-1 pCV1. Purified TAT protein but not TAT toxoid exhibited a strong biologic activity as measured by the CAT assay on HeLa cells. The activity of native TAT was inhibited by murine anti-TAT antibodies. Inactivation of Tat toxoid was evaluated by absence of reactivity tested by CAT assay (Le Buanee et al.; Gringeri et al., 1998).

Immunization Protocol

Tat toxoid (70 µg) in phosphate-buffered saline (PBS, 0.4 mL) emulsified with IFA (0.4 mL), was injected intramuscularly from 1 to 3 times at 1-month intervals, to ascertain immunogencity with different vaccine schemes and safety after multiple injections.

Serum and peripheral blood mononuclear cells (PBMCs) were separated from blood collected prior to the first injection (control) and 8 days after each injection.

Study Subjects

Five healthy volunteers (3 men, 2 women), between 25 and 46 years of age, were enrolled (A-B, Table 9). HIV-1 antibody negativity was tested by enzymed-linked immunosorbent assay (ELISA) with confirmatory Western blot test. Inclusion criterian were absence of active or chronic diseases, age between 18 and 65 years reliability to adopt preventive measures to prevent HIV-1 infection no exposure to risk of HIV-1 infection, in the previous 3 months, no active signs or symptoms of any acute disease, and signed informed consent. Two more study subjects with the same characteristics (1 man, 1 woman) were enrolled as controls (F and G, Table 9).

One subject received a single injection of TAT toxoid vaccine intramuscularly. These study subjects were primed with two injections of the same preparation and the remaining study subject received TAT toxoid three times.

Any signs and symptoms were carefully investigated by clinical examination and interviews over the first 7 days after each injection and monthly thereafter for the entire 6-month follow-up period. Complete blood cell counts, T-cell phenotype, and renal and liver function tests were carried out before and after immunization.

Immunogencity

The humoral response to Tat toxoid relied on the determination by ELISA of circulating anti-Tat antibody levels on sera collected between 7 and 14 days after each injection and monthly thereafter using biologically active recombinant Tat as the detecting antigen.

The serum anti-Tat antibodies were detected by standard ELISA assay using Costar (Cambridge, Mass., U.S.A.) plates (FB, 96 wells 3590). Tat recombinant protein was fixed on the plate at 50 ng/well. Sera at 1:500 dilution were tested according in the standard ELISA procedure and the results were expressed as optical density (OD) values. Study protocol defined as responders those study subjects showing an increase of anti-HIV-1 TAT antibody levels of twofold or more from preimmunization values. This cutoff is based on the observation of HIV-1-infected but not immunized patients (>100 study subjects tested), who did not exhibit variability in their Tat antibody levels (less than ±1.5-fold) in consecutive serum samples collected over a 1-year period and tested in a same experiment (under the same ELISA measurements) Anti-Tat antibodies titration was done 4 to 6 months after the first injection and expressed as the highest dilution giving a positive reaction measurable by ELISA.

Assessment of the cellular response relied on both delayed-type hypersensitivity (DTH) response toward HIV-1 TAT protein and on in vitro cell-mediated Immunity (CMI) by T-cell proliferation of Tat toxoid-stimulated PBMCs measured by $^3$H thymidine incorporation test. Fresh PBMCs from study subjects were cultured for 6 days in 96-well round-bottom culture plates in the presence (test samples) or absence (control samples) of 10 µg/ml of Tat toxid. At 18 hours before completion of the culture, 0.5 µCi of thymidine was added to each well. Cells were then harvested and thymidine incorporated in cell DNA was measured in a β-counter and expressed as counts-per-minute per milliliter (cpm/ml). Results were expressed as proliferation index (PI). PI=cpm in test samples: cmp in control samples. A PI>1 was considered positive (Picard et al., 1990).

Administration of intradermal injection of Tat toxoid (10 µg) in 100 µl PBS was carried out for the DTH skin test before anti-Tat vaccination and after immunization. Positive skin test results corresponded in a papula of >0.5 cm in diameter measured after 48 to 72 hours.

Results

Safety and Tolerance

Administration of the Tat toxoid preparation one to three times did not result in any untoward local or systemic reactions and was well tolerated by all the subjects. Even the study subject who received three intramuscular injections of the water-in-oil emulsion did not complain about local pain or any other discomfort. No change in complete blood cell counts and T-cell phenotypes, or in renal and liver fuction tests was observed in any of the patients.

Humoral Response

Figure 5A:
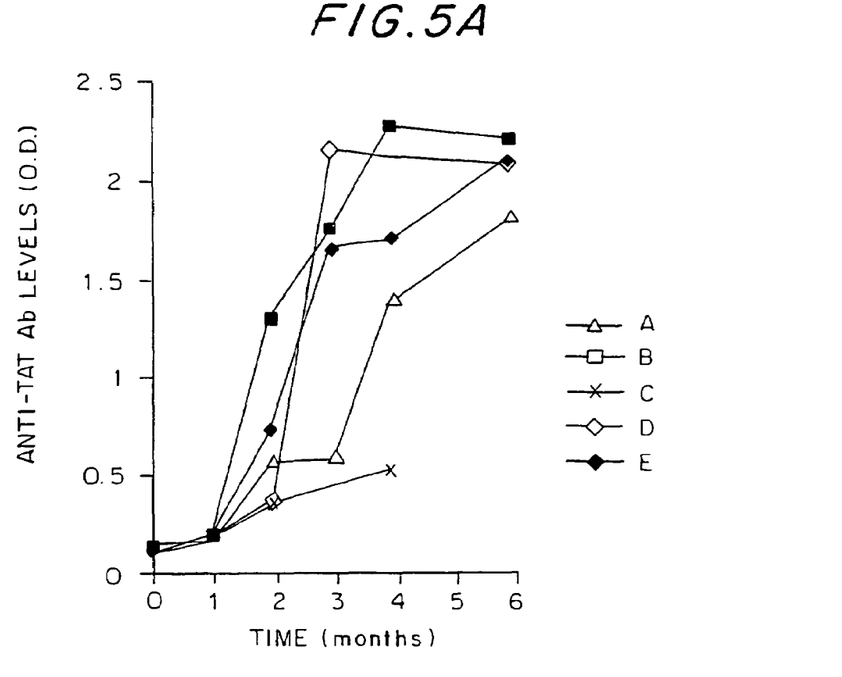
Figure 5B:
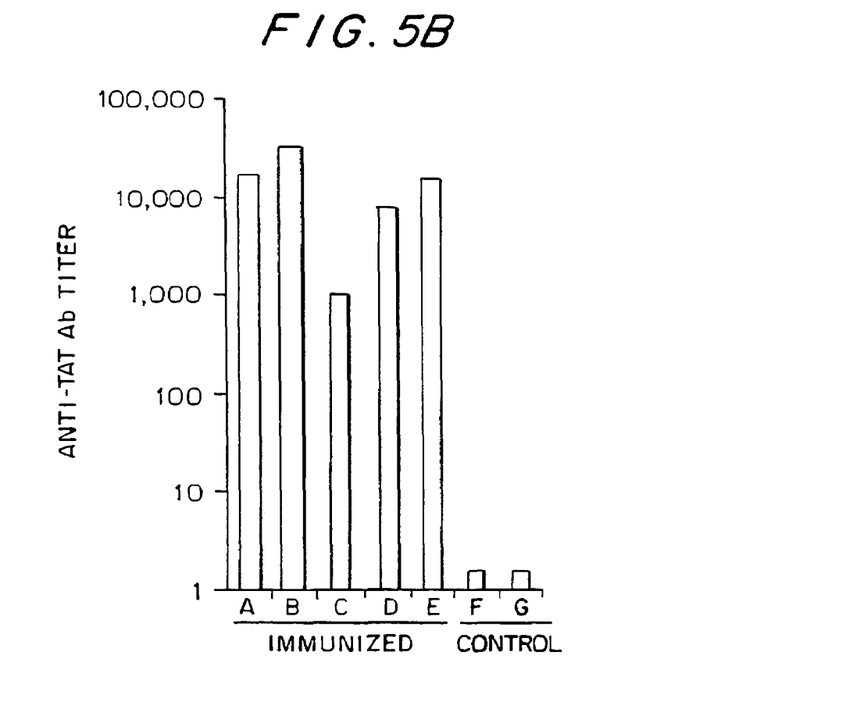

The 5 immunized study subjects exhibited high anti-Tat antibody levels in their serum following the first, second, and/or third injection (FIGS. 5A and 5B) with an increase of antibody levels ranging from threefold to more than 10-fold from preimmunization values. No detectable anti-Tat antibody levels were shown by ELISA in control study subjects (<0.250 OD). After 4 to 6 months from the first immunizing injections, 5 of 5 immunized study subjects exhibited high titers of anti-Tat antibodies ranging from 1:1,000 to 1:64,000 (FIG. 5B, Table 9), whereas no dectable titers were found in controls (<1:250). The subjects exhibiting the highest level of anti-Tat antibodies should be those that will have better protection against HIV-1 infection.

Cellular Response

The 4 tested study sujects showed a positive DTH response to Tat characterized by a well-formed 1- to 3-cm red papula occurring at 48 hours following intradermmal injection of Tat toxoid and persisting at 72 hours (Table 9), whereas no skin reaction was observed in control study subjects.

Cell-mediated immunity, as measured by T-cell proliferation of PBMCs following Tat toxoid stimulation was also markedly increased in the 5 immunized individuals but not in nonimmunized voluteers (Table 9). Proliferation index varied from 6 to 63 in vaccinees, whereas it was <1.5 in controls.

toxoid in healthy HIV-1-seronegative study subjects. An inactivated but immunogenic Tat (i.e., Tat toxiod) was used as immunogen to avoid damages induced by native Tat on various tissues including the CNS (Shi et al., 1998) and the immune system (viscidi et al., 1989), to which introduction of Tat toxin might introduce hazards particularly in those study subjects with an autoimmune predisposition or those whose immune systems were compromised by chronic infections, chronic parasitic infestation, or as a result of malnutrition. Immunization with Tat toxoid, in a water-in-oil emulsion, was safe and well-tolerated by all seronegative study subjects.

Anti-Tat immunization induced high levels of circulating anti-Tat antibodies in all immunized study subjects; this antibody response was achieved even after one immunizing injection and was accompanied by a cellular resonse, as shown by T-cell proliferation in vitro and by skin test in vivo. Furthermore, individuals A, B, and E, who were first immunized 1 year previously, continued to maintain a high titer of circulating Tat toxin antibodies ($16,000^{-1}$, $8,000^{-1}$ and $16,000^1$, respectively). Of interest in individual D, who was immunized at the same time with Nef toxoid and p24 protein, the titers of circulating antibodies and the cellular response directed against these HIV-1 antigens increased greatly (data not shown), as well as those directed against Tat (Table 9).

In conclusion, the presence of high levels of circulating anti-Tat antibodies should antiagonize Tat toxin released into the extracellular compartment by infected cells and should thus prevent the Tat-induced immunosuppression of uninfected T cells. Thus, following HIV-1 exposure of uninfected individuals immunized with Tat toxoid and other CMI-inducing HIV-1 antigens, such as Env, Gag or Nef peptides, the presence of high levels of circulating antibodies against Tat should control the immunosuppressive effect of Tat toxin released during acute infection and allow the cellular response induced by HIV-1 structural antigens to develop. The almost immediate release of high level of β-chemokines could contribute to enhancement of the host

TABLE 9

Immune response of seronegative study subjects to Tat toxoid

| | | | CD4 cell count (%)[a] | | Tat toxoid | | | |
|---|---|---|---|---|---|---|---|---|
| Subjects | Age (y) | Gender | T0 | T1 | injections | DTH[b] | Anti-Tat Ab titer[c] | CMI[d] |
| A | 46 | F | 40.9 | 44.9 | 2 | + | 16,000 | 63 |
| B | 43 | M | 50.8 | 52.1 | 1 | + | 32,000 | 11 |
| C | 25 | F | 49.0 | 44.1 | 2 | NA | 1,000 | 6 |
| D | 29 | M | 37.0 | 31.9 | 3 | + | 8,000 | 32 |
| E | 35 | M | NA | NA | 2 | + | 16,000 | 10 |
| F | 30 | M | 48.5 | 43.6 | 0 | − | <250 | 1.2 |
| G | 32 | F | 43.8 | 42.2 | 0 | − | <250 | 1.0 |

[a]T0, preimmunization values: T1, values 4 to 6 months after the first immunizing injection.
[b]Delayed-type hypersensitivity test was performed by Intradermal injection of Tat toxoid (0.5 μg in 100 μl).
[c]Anti-Tat Ab titers were tested on serum samples collected 4–6 months after the first injection.
[d]Cell-mediated immunity was assessed by T-cell proliferation measured by $^3$H thymidine incorporation. Results are given as proliferation index (PI). PI = cpm (dxp):cpm (control).
NA not available: DTH, delayed-type hypersensitivity: CMI, cell-mediated immunity: Ab, antibody: cpm, counts per minute.

Discussion

This open, controlled study was designed to evaluate safety and immunogenicity of an active immuniztion against HIV-1 Tat protein using an inactiviated recombinant Tat resistance to HIV-1 infection (Zagury et al., 1998). A phase II/III trial will be conducted to confirm these assertions.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Achour et al, "HGP-30, a synthetic analogue of human immunodeficiency virus (HIV-1) p17, is a target for cytotoxic lymphocytes in HIV-1-infected individuals" *Proc. Natl. Acad. Sci. USA* 87:7045–7049 (1990)

Borrow et al, "Antiretroviral pressure exerted by HIV-1-specific cytotoxic T lymphocytes (CTLs) during primary infection demonstrated by rapid selection of CTL escape virus" *Nat. Med.* 3:205–211 (1997)

Chirmule et al, "Human immunodeficiency virus tat induces functional unresponsiveness in T cells" *J. Virol.* 69:492–498 (1995)

Cullen, "Regulation of HIV-1 gene expression" *FASEB J.* 5:2361–2368 (1991)

Ensoli et al, "Release, uptake, and effects of extracellular human immunodeficiency virus type 1 tat protein on cell growth and viral transcription" *J. Virol.* 67:277–287 (1993)

Gallo et al, "Frequent detection and isolation of cytopathic retroviruses (HTLV-III) from patients with AIDS and at risk of AIDS" *Science* 224:500–503 (1984)

Goulder et al, "Late escape from an immunodominant cytotoxic T-lymphocyte response associated with progression to AIDS" *Nat. Med.* 3:212–217 (1997)

Goulder et al., "Novel, cross-restricted, conserved, and immunodominant cytotoxic T lymphocyte epitopes in slow/non-progressors in HIV-1 type 1 infection" *AIDS Res. Hum. RetrovirusesU* 12:1691–1698 (1996)

Gringeri et al, "Safety and immunogenicity of HIV-1 tat toxoid in immunocompromised HIV-1-infected patients" *J. of Human Virology* (1998)

Hendel et al, "Contribution of cohort studies in understanding HIV-1 pathogenesis: introduction of the GRIV cohort and preliminary results" *BioMedicine and Pharmacol.* 50:480–487 (1996)

Hynes, "Integrins: a family of cell surface receptors" *Cell* 48:549–554 (1987)

Hynes, "Integrins: versatility, modulation, and signaling in cell adhesion" *Cell* 69:11–25 (1992)

Katsikis et al, "HIV-1 type 1 tat protein enhances activation but not Fas (CD95) induced peripheral blood T cell apoptosis in healthy individuals" *Int. Immunol.* 9:835–841 (1997)

Krone et al., "Natural antibodies to HIV-1-tat epitopes and expression of HIV-1 genes in vivo" *J. Med. Virol.* 26:261–270 (1988)

Le Buanee et al., "Prophylactic and therapeutic AIDS vaccine containing as a component the innocuous Tat toxoid" *Biomed Pharm/AIDS Sci.* 52:431–5 (1998)

Li et al, "Induction of apoptosis in uninfected lymphocytes by HIV-1 tat protein" *Science* 268:429–431 (1995)

Li et al, "tat protein induces self-prepetuating permissivity for productive HIV-1 infection" *Proc. Natl. Acad. Sci. USA* 93:14720–14725 (1997)

Lolli et al., "Effect of antibody to HIV-1 tat protein on viral replication in vitro and progression of HIV-1 disease in vivo" *J. Acquir. Immune Defic. Syndr. Hum. Retrovirol"* 10:408–416 (1995)

Nixon et al, "CTL reconition of HIV-1 proteins and peptides" *AIDS* 5:1055–1056 (1991)

Picard et al, "A 2-year follow-up of an anti-HIV-1 immune reaction in HIV-1 gp160-immunized healthy seronegative humans: evidence for persistent celll-mediated immunity" *JAIDS* 5:539–546 (1992)

Rappaport et al, "32 bp CCR5 gene deletion and resistance to fast progression among HIV-1 infected heterozygotes" *The Lancet* 349:922–923 (1997)

Reiss et al., "Contribution of antibody response to recombinant HIV-1 gene-encoded products nef, rev, tat, and protease in predicting development of AIDS in HIV-1-infected individuals" *J. Acquir. Immune Defic.* (1991)

Shi et al., "Apoptosis induced by HIV-1 Tat protein and TNF-alpha: Potentiation of neurotoxicity mediated by oxidative stress and implications for HIV-1 dementia" *J. Neuroviral* 4:281–90 (1998)

Viscidi et al, "Inhibition of antigen-induced lymphocyte proliferation by tat protein from HIV-1" *Science* 246:1606–1608 (1989)

Weeks et al, "Identification of a novel cell attachment domain in the HIV-1 tat protein and its 90-kDa cell surface binding protein" *J. Biol. Chem.* 268:5279–5284 (1993)

Westendorp et al, "Sensitization of T cells to CD95-mediated apoptosis by HIV-1 tat and gp120"*Nature* 375:497–500 (1995)

Zagury, "A naturally unbalanced combat" *Nat. Med.* 3:156–157 (1997)

Zagury et al, "Long-term cultures of HTLV-III-infected T cells: a model of cytopathology of T-cell depletion in AIDS" *Science* 231:850–853 (1986)

Zagury et al, "Model of AIDS immunopathogenesis based on the HIV-1 gp120 and tat-induced dysregulation of uninfected immune cells" *Cellular Pharmacology* 3:123–128 (1996)

Zagury et al, "IFNα and tat involvement in the immunosuppression of uninfected T cells and C—C chemokine decline in AIDS" *Proc. Natl. Acad. Sci. USA* 1998a (in press)

Zagury et al, "C—C chemokines, pivotal in protection against HIV-1 infection" *Proc. Natl. Acad. Sci. USA* 1998b (in press)

Zhang et al, "Protective immunity to HIV-1 in SCID/beige mice reconstituted with peripheral blood lymphocytes of exposed but uninfected individuals" *Proc. Natl. Acad. Sci. USA* 93:14725–14725 (1996)

What is claimed is:

1. A method for determining the prognosis of an HIV infected individual, comprising:
   measuring the levels of anti-tat antibodies and p24 protein in the serum of an HIV infected individual;
   comparing the measured levels to a mean anti-tat antibody value and a mean p24 protein value; and
   determining the prognosis of the HIV infected individual, wherein anti-tat antibody levels above the mean value in combination with p24 protein levels below the mean value is indicative of disease non-progression towards AIDS, and anti-tat antibody levels below the mean value in combination with p24 protein levels above the mean level is indicative of disease progression towards AIDS.

2. The method of claim 1, wherein the HIV infected individual is a non-progressor who has been seropositive for HIV for over eight years, is clinically asymptomatic in the absence of antiretroviral therapy, and does not have a CD4 cell count below 500/mm$^3$.

* * * * *